United States Patent
Snell et al.

(10) Patent No.: US 8,214,033 B2
(45) Date of Patent: Jul. 3, 2012

(54) INTERFERENTIAL CARDIAC PRECONDITIONING AND DEPOLARIZATION

(75) Inventors: Jay Snell, Studio City, CA (US); Mary Elizabeth Bush, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 408 days.

(21) Appl. No.: 12/265,579

(22) Filed: Nov. 5, 2008

(65) Prior Publication Data

US 2010/0114207 A1    May 6, 2010

(51) Int. Cl.
*A61N 1/00* (2006.01)

(52) U.S. Cl. .................. 607/5; 607/28; 607/67

(58) Field of Classification Search ........ 607/4–36, 607/66–69
See application file for complete search history.

(56) References Cited

U.S. PATENT DOCUMENTS

| | | | |
|---|---|---|---|
| 3,775,658 A * | 11/1973 | Miles ............................... 607/5 |
| 5,776,173 A * | 7/1998 | Madsen et al. .................. 607/67 |
| 5,792,187 A | 8/1998 | Adams |
| 6,006,131 A | 12/1999 | Cooper et al. |
| 6,067,470 A * | 5/2000 | Mower .............................. 607/5 |
| 6,091,989 A | 7/2000 | Swerdlow et al. |
| 6,317,631 B1 * | 11/2001 | Ben-Haim et al. ................ 607/9 |
| 6,411,844 B1 * | 6/2002 | Kroll et al. ......................... 607/5 |
| 6,470,211 B1 * | 10/2002 | Ideker et al. ....................... 607/5 |
| 6,658,294 B1 * | 12/2003 | Zadeh et al. .................... 607/28 |
| 6,745,073 B1 | 6/2004 | Kroll |
| 6,754,525 B1 * | 6/2004 | Province et al. .................. 607/4 |
| 6,826,429 B2 * | 11/2004 | Johnson et al. ................ 607/67 |
| 2002/0165590 A1 | 11/2002 | Crowe et al. |
| 2004/0143297 A1 * | 7/2004 | Ramsey, III ...................... 607/5 |
| 2005/0107834 A1 * | 5/2005 | Freeman et al. .................. 607/5 |
| 2005/0278001 A1 | 12/2005 | Qin et al. |
| 2007/0219598 A1 * | 9/2007 | Rhodes ........................... 607/67 |
| 2010/0280366 A1 * | 11/2010 | Arne et al. ..................... 600/425 |

FOREIGN PATENT DOCUMENTS

| WO | 02068040 A2 | 9/2002 |
| WO | 02068040 A3 | 9/2002 |
| WO | 2005122740 A2 | 12/2005 |
| WO | 2005122740 A3 | 12/2005 |

* cited by examiner

*Primary Examiner* — Niketa Patel
*Assistant Examiner* — Catherine Voorhees

(57) ABSTRACT

Exemplary systems, devices, and methods pertaining to cardiac related therapy and particularly to interferential cardiac preconditioning and depolarization are described. A cardiac arrhythmia is detected from electrogram data sensed from a patient's heart and a region of the heart affected by the cardiac arrhythmia is determined. The affected region is interferentially energized by multiple cycles of two concurrently delivered alternating currents which are offset in frequency.

10 Claims, 4 Drawing Sheets

INTERFERENTIAL CARDIAC PRECONDITIONING AND DEPOLARIZATION

FIELD OF THE INVENTION

The subject matter presented herein generally pertains to cardiac related therapy and particularly to interferential cardiac preconditioning and depolarization.

BACKGROUND

Techniques for so-called "direct current" (DC) cardiac defibrillation have not changed significantly in many decades. Conventional DC cardiac defibrillation techniques deliver shocking pulses at relatively high voltages (e.g., typically over 300 V) to ensure adequate depolarization of the patient's cardiac tissue. While the pulses may be delivered in multiple phases (e.g., biphasic or triphasic) in an effort to minimize tissue damage, they are still referred to as DC. Regardless of multiphase delivery, the relatively high voltage can still produce undesirable hyper-polarization of cardiac tissue and/or depolarization of adjacent thoracic skeletal muscles and nerves. Among other disadvantages, the depolarization of the adjacent thoracic skeletal muscles and nerves can cause extreme patient discomfort.

SUMMARY

Exemplary systems, devices, and methods pertaining to cardiac related therapy and particularly to interferential cardiac preconditioning and depolarization are described. One method detects a cardiac arrhythmia from electrogram data sensed from a patient's heart and determines a region of the heart affected by the cardiac arrhythmia. The method also interferentially energizes the affected region. The method further monitors electrogram data from the patient to determine whether the arrhythmia converted to a more normal rhythm.

Another implementation is manifested as a medical device that includes a mechanism for detecting a cardiac arrhythmia. The medical device also includes a mechanism for delivering an interferential therapy to cardiac tissue affected by the arrhythmia, wherein the interferential therapy comprises multiple cycles of two concurrently delivered alternating current (AC) waveforms having a frequency difference of about 50 hertz to about 200 hertz.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

DETAILED DESCRIPTION

Overview

Various exemplary techniques, methods, devices, systems, etc., described herein pertain to medical devices and techniques for interferential cardiac preconditioning and depolarization. In some cases, some or all of the techniques are implemented by a medical device that is external to a patient, while in other cases some or all of the techniques are implemented by an implantable medical device (IMD), such as implantable cardioverter-defibrillator (ICD).

Interferential stimulation and preconditioning of cardiac tissue utilize superposition of two medium to high frequency AC signals that are offset by a relatively small frequency. The signals may be sinusoidal or of other shape. For example, the signals may be generated using rapid switching of otherwise DC signals to achieve two or more medium to high frequency that include a relatively small frequency offset. Hence, chopped DC may simulate AC. Of course, the interference pattern would change, depending on the original waveforms. Also, the two waveforms, in addition to being different frequency, need not be the same shape. For example, one may be sinusoidal AC and the other generated by chopping a capacitive discharge waveform (DC).

As described herein, superposition of two signals offset by some frequency creates a beat frequency corresponding to the offset as the two signals go in and out of phase. The delivery of these signals to the body can precondition cardiac tissue for subsequent shocking. For example, in some cases, interferential preconditioning energizes target cardiac tissue sufficiently to lower the cardiac tissue's activation threshold but not to depolarize the cardiac tissue. With sufficient preconditioning, a relatively low energy DC signal can then be utilized to depolarize the cardiac tissue. Stated another way, interferential preconditioning can lower the energy required for depolarization of targeted cardiac tissue. In other implementations, a beat frequency is utilized to energize and depolarize target cardiac tissue. As described herein, such a technique can depolarize to effectively stimulate or shock cardiac tissue as would be achieved through conventional techniques; noting that preconditioning aims to reduce energy requirements. For instance, in the case of cardiac arrhythmias, delivery of interferential signals can energize the target cardiac tissue sufficiently to cause depolarization leading to cardioversion or ventricular defibrillation.

Exemplary IMD

The techniques described below can be implemented in connection with any IMD that is configured or configurable to sense cardiac data and/or provide cardiac therapy.

Figure 1:
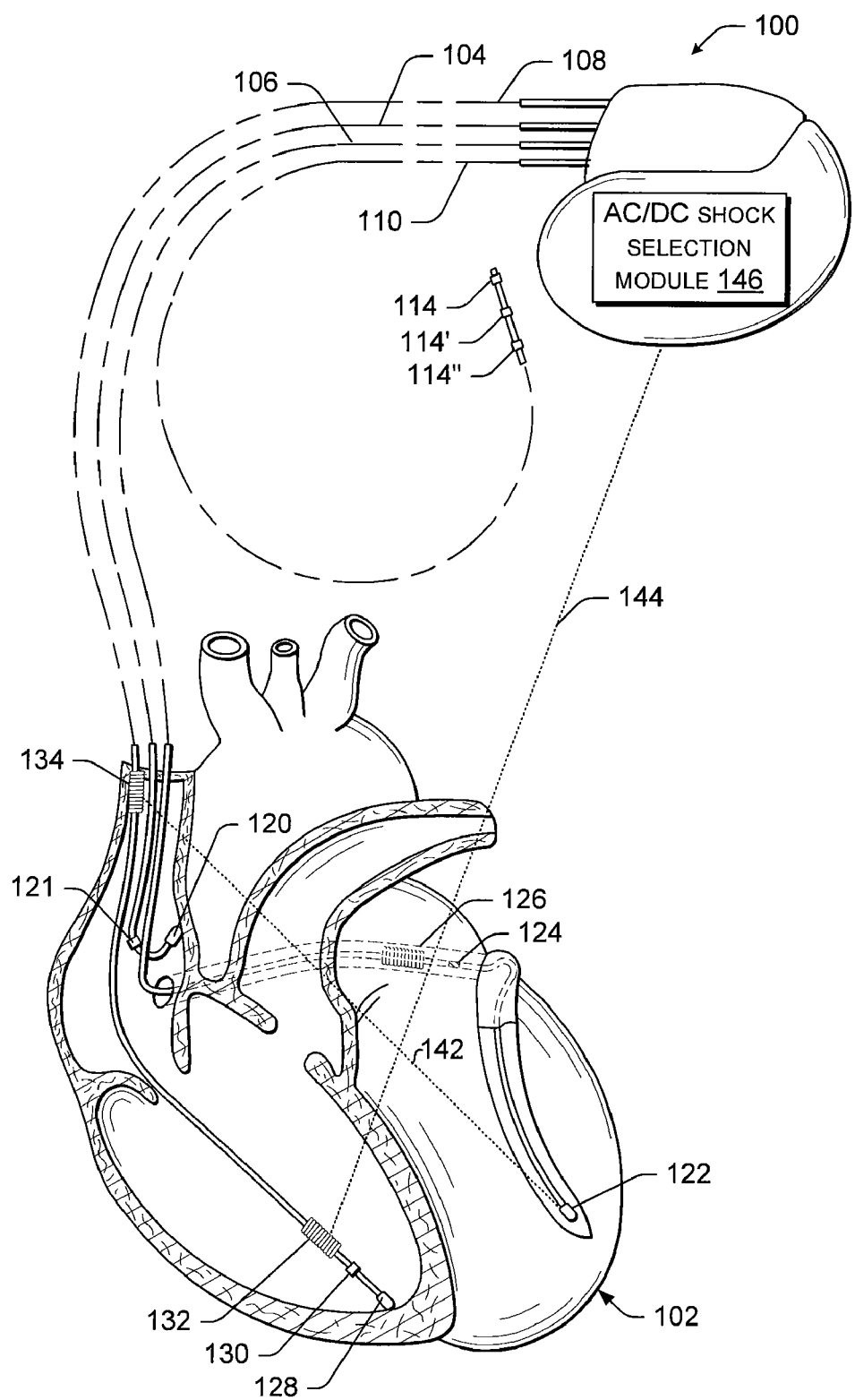
FIGS. 1-2 are simplified diagrams illustrating exemplary implantable medical devices (IMDs) operable to employ techniques for interferential cardiac preconditioning and depolarization in accordance with one implementation.

FIG. 1 shows an exemplary IMD 100 in electrical communication with a patient's heart 102 by way of three leads 104, 106, 108, suitable for delivering multi-chamber stimulation and shock therapy utilizing direct current (DC) signals. Alternatively or additionally, the IMD 100 is operable for effecting patient therapy by delivering multiple simultaneous alternating current (AC) signals.

The leads 104, 106, 108 are configurable for delivery of stimulation pulses suitable for stimulation of autonomic nerves, non-myocardial tissue, other nerves, etc. In addition, IMD 100 includes a fourth lead 110 having, in this implementation, three electrodes 114, 114', 114" suitable for stimulation of autonomic nerves, other nerves, myocardial tissue, non-myocardial tissue, etc. For example, this lead may be positioned in and/or near a patient's heart or near an autonomic nerve within a patient's body and remote from the heart. In another example, the fourth lead can be configured to sense the phrenic nerve as a means of sensing activation of the diaphragm. The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the IMD 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. In an alternative configuration, lead 110 can be replaced with a mechanism for connecting the IMD to various other devices. For example, the mechanism can facilitate connecting IMD 100 to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. The coronary sinus lead 106 further optionally includes one or more other electrodes for any of a variety of purposes (e.g., sensing, stimulation, etc.). For example, an exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Alternatively or additionally, the above described leads and electrodes (and or other dedicated leads and/or electrodes) can be utilized for delivering AC signals. In this case, the AC signals are delivered in a manner that instigates interferential stimulating, shocking and/or preconditioning. Interferential stimulating, shocking and/or preconditioning is accomplished by delivering at least two concurrent AC signals. The AC signals can have medium to high frequencies such as in the 1 kHz to 500 kHz range. Some implementations can utilize AC signals in the 1,000-6,000 hertz range and have a frequency difference (e.g., offset) between the two AC signals of about 50 hertz to about 200 hertz. For instance, in one example, the first signal can have a frequency of 2,000 hertz and the second signal can have a frequency of 2,100 hertz. As mentioned, switching or other techniques may be used to achieve the medium to high "AC" frequencies.

The AC signals are delivered via electrodes interposed around the target tissue to create at least two pathways that intersect (or at least approach) one another proximate the target tissue. For instance, in the illustrated configuration of FIG. 1 for AC signals targeting the left and/or right atria, a first AC signal can be delivered along a first pathway 142 and a second AC signal can be delivered along a second pathway 144. Continuing with the above example, assume that the first AC signal has a frequency of 2,000 hertz and the second AC signal has a frequency of 2,100 hertz.

The AC signals may be viewed as traveling along pathways in the body, which depends on the position/placement of electrodes and the composition of the body between any corresponding electrodes. As mentioned, intersection of two AC signals (with a frequency offset) along a first pathway and a second pathway creates an interferential beat frequency that depends on the offset (e.g., from about 30 hertz to about 120 hertz) that can be utilized for atrial defibrillation and/or atrial preconditioning. In general, for the human body and heart a maximum in effectiveness occurs somewhere between 30 hertz and 120 hertz, typically around 60 hertz.

In one example, the first pathway 142 is generated by AC signals between the SVC coil electrode 134 and the LV tip electrode 122. The second pathway 144 is generated by AC signals between the RV coil electrode 132 and a housing of the IMD. (The IMD housing is designated with specificity in FIG. 2). In another example, the first pathway extends between an electrode positioned in the right atrial appendage such as electrode 120 and an electrode positioned distally in the coronary sinus while the second pathway extends between the coronary sinus os and the left subclavian vein. Several other examples utilize the same first pathway that extends between the right atrial appendage and the coronary sinus while the second pathway is selected as extending between one of coronary sinus os and the pulmonary artery, IMD housing and SVC, and/or IMD housing and the right ventricle.

In general, the polarity of the electrodes involved in delivering AC signals will have little effect. This is in contrast to effects seen for DC stimulation and shocking, wherein capture threshold differ depending on whether pacing is anodal or cathodal. Various techniques may be employed where specialized electrodes, electrode arrays, antennas, etc., act to focus the AC signals to, for example, target specific tissue. Such techniques may be used to focus preconditioning energy or vary the energy deposition with respect to time over some region or regions.

In general, at a minimum, two pairs of electrodes (e.g., quad electrode array) deliver the preconditioning energy. Such electrodes may be internal (in vivo) or external (including skin mounted). Where signals can be slightly offset in time, a configuration may rely on less than four electrodes. For example, a configuration may rely on a can electrode with two coils where a microsecond delay occurs between one AC signal delivered at a first frequency and another AC signal delivered at a second frequency (offset from the first frequency). In general, a time delay between deliveries of two AC signals is small compared to the period of the AC frequencies. Such an approach allows for electrical circuits of various configurations and can minimize the number of electrodes required.

Several pathway options exist for AC signals targeting the left and/or right ventricles. In a first such example, a first pathway can extend between the RV and the SVC while the second pathway extends between the IMD housing and the coronary sinus (os or distal). In another example the first pathway extends between the RV and the coronary sinus (os or distal) and the second pathway extends between the IMD housing and the SVC. The skilled artisan should recognize other electrode placement configuration for achieving desire pathways for atrial and/or ventricular treatment consistent with the concepts described above and below. For example, some implementations can employ dedicated electrodes for delivering the AC signals.

IMD 100 further includes an AC/DC shock selection module 146 that is operable to ascertain when a detected patient condition warrants one or both of atrial and ventricular shock therapy. In such an instance, AC/DC shock selection module is operable to select an appropriate shocking therapy including DC shock therapy, AC shock therapy, and DC shock therapy with AC preconditioning. AC preconditioning can be considered as a therapy that energizes the target tissue without causing depolarization. A DC shock of lower than normal power can then sufficiently depolarize the target tissue. AC/DC shock selection module 146 is described in more detail below in relation to FIG. 2.

Figure 2:
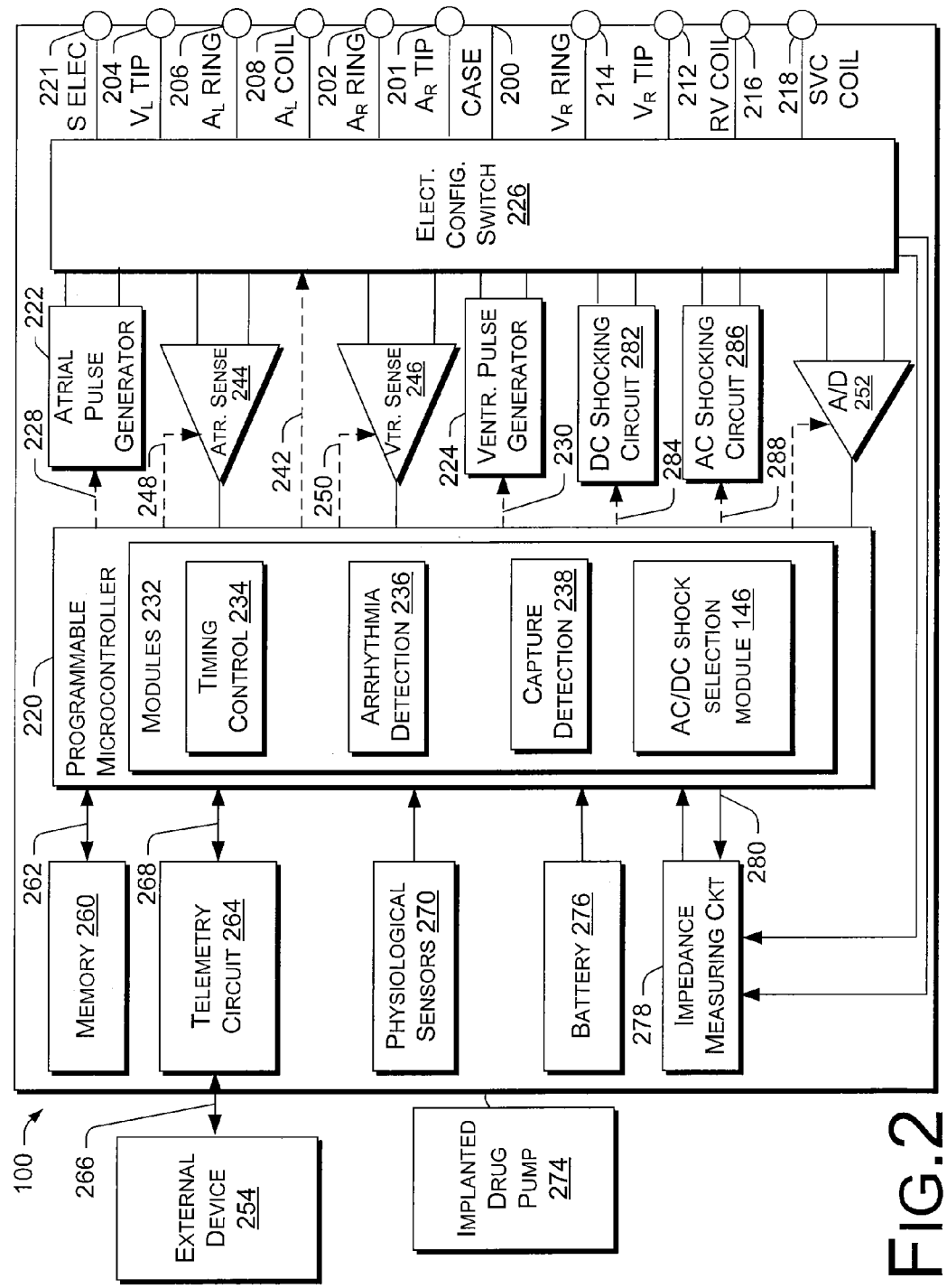

FIG. 2 shows an exemplary, simplified block diagram depicting various components of IMD 100. The IMD 100 can be capable of treating both fast and slow arrhythmias with stimulation therapy, including cardioversion, defibrillation, and pacing stimulation. The IMD can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for IMD 100 is often referred to as the "can", "case" or "case electrode", and may be programmably selected to act as the return electrode for all "unipolar" modes. Housing 200 may further be used as a return electrode alone or in combination with one or more of the coil electrodes 126, 132, and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 201 adapted for connection to the atrial tip electrode 120. A right atrial ring terminal ($A_R$ RING) 202 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right ventricular sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the IMD 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller(s) 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators 222, 224 may include dedicated, independent pulse generators, multiplexed pulse generators, or shared pulse generators. The pulse generators 222, 224 are controlled by the microcontroller 220 via appropriate control signals 228, 230, respectively, to trigger or inhibit the stimulation pulses.

Microcontroller 220 further includes a plurality of modules 232 that, when executed, perform various functions of the IMD. For instance, the modules can perform arrhythmia detection, timing control, and/or morphology detection, among other functionalities.

The illustrated example specifically designates a timing control module 234, an arrhythmia detection module 236, a capture detection module 238, and AC/DC shock selection module 146. Timing control module 234 controls the timing of the stimulation pulses (e.g., pacing rate, atrioventricular (AV) delay, atrial interconduction (A-A) delay, or ventricular interconduction (VV) delay, etc.) and keeps track of the timing of refractory periods, blanking intervals, noise detection windows, evoked response windows, alert intervals, marker channel timing, etc., which is well known in the art.

The arrhythmia detection module 236 and the capture detection module 238 can be utilized by the IMD 100 for detecting patient conditions and determining desirable times to administer various therapies such as pacing, defibrillation and/or in vivo dispensing of pharmaceuticals. AC/DC shock selection module 146 is operable to ascertain when a detected patient condition warrants one or both of atrial and ventricular shock therapy. In such an instance, AC/DC shock selection module 146 is operable to select an appropriate shocking therapy including DC shock therapy, AC shock therapy, and DC shock therapy with AC preconditioning. The aforementioned modules may be implemented in hardware as part of the microcontroller 220, or as software/firmware instructions programmed into the device and executed on the microcontroller 220 during certain modes of operation. Alternatively, any of the described modules could be implemented as stand alone components such as an application specific integrated circuit (ASIC) that communicates with other IMD components.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines which electrodes will be involved in delivering the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits 244, 246 may include dedicated sense amplifiers, multiplexed amplifiers, or shared amplifiers. Switch 226 determines which electrodes are involved in cardiac sensing by selectively closing the appropriate switches, as is also known in the art. In this way, the clinician may choose the electrodes used for sensing independent of the electrodes used for stimulation. The sensing circuits (e.g., 244 and 246) are optionally capable of obtaining information indicative of tissue capture.

Each sensing circuit 244, 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation.

The outputs of the atrial and ventricular sensing circuits 244, 246 are connected to the microcontroller 220, which, in turn, is able to trigger or inhibit the atrial and ventricular pulse generators 222, 224, respectively, in a demand fashion in response to the absence or presence of cardiac activity in the appropriate chambers of the heart. Furthermore, as described herein, the microcontroller 220 is also capable of analyzing information output from the sensing circuits 244, 246 and/or the analog-to-digital (A/D) data acquisition system 252 to determine or detect whether capture has occurred and to program a pulse, or pulses, in response to such determinations. The sensing circuits 244, 246, in turn, receive control signals over signal lines 248, 250 from the microcontroller 220 for purposes of controlling the gain, threshold, polarization charge removal circuitry (not shown), and the timing of any blocking circuitry (not shown) coupled to the inputs of the sensing circuits 244, 246, as is known in the art.

For arrhythmia detection, IMD 100 utilizes the atrial and ventricular sensing circuits 244, 246 to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation) are then classified by the arrhythmia detector 236 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of the A/D data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy.

Advantageously, the operating parameters of the IMD 100 may be non-invasively programmed into the memory 260 through a telemetry circuit 264 in telemetric communication via two-way communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The IMD 100 can further include a physiologic sensor(s) 270 to detect one or more of patient activity, patient posture, and respirations, among others. Microcontroller 220 can utilize data received from the physiologic sensor(s) 270 to adjust the various pacing parameters (such as rate, AV Delay, VV Delay, etc.) at which the atrial and ventricular pulse generators 222, 224 generate stimulation pulses. Microcontroller 220 further can utilize data received from the physiologic sensor(s) 270 to identify patient postures that can be correlated with measured thoracic impedance values.

While shown as being included within the IMD 100, it is to be understood that the physiologic sensor 270 may also be external to the IMD 100, yet still be implanted within or carried by the patient. Examples of physiologic sensors that may be implemented in IMD 100 include known sensors that, for example, sense pressure, respiration rate, pH of blood, cardiac output, preload, afterload, contractility, oxygen levels, and so forth. Another sensor that may be used is one that detects activity variance, where an activity sensor is monitored to detect the low variance in the measurement corresponding to the sleep state and/or maintenance of a specific posture.

The physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's posture and activity status, such as whether the patient is climbing upstairs or descending downstairs or whether the patient is sitting up after lying down.

The IMD 100 optionally includes circuitry capable of sensing heart sounds and/or vibration associated with events that produce heart sounds. Such circuitry may include an accelerometer as conventionally used for patient position and/or activity determinations. While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

IMD 100 may also include, or be in communication with, an implanted drug pump 274 or other drug delivery mechanism to effect patient therapy. The drug pump can be activated in various scenarios, such as when a heart failure condition is detected by thoracic impedance/physiology correlation module 240.

The IMD 100 additionally includes a battery 276 that provides operating power to all of the circuits shown in FIG. 2. For the IMD 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 can further include magnet detection circuitry (not shown), coupled to the microcontroller 220, to detect when a magnet is placed over the IMD 100. A magnet may be used by a clinician to perform various test functions of the IMD 100 and/or to signal the microcontroller 220 that the external programmer 254 is in place to receive or transmit data to the microcontroller 220 through the telemetry circuits 264. Trigger IEGM storage also can be achieved by magnet.

The IMD 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and via AC/DC shock selection module 146, automatically applies an appropriate therapy to the heart aimed at terminating the detected arrhythmia. To this end, the microcontroller 220 further controls a DC shocking circuit 282 by way of a control signal 284 and/or an AC shocking circuit 286 by way of a control signal 288. The DC shocking circuit can employ various mechanisms such as capacitors to generate DC shocking pulses. When capacitors are employed the DC shocking pulses can have known pulse decay characteristics. DC pulses may be monophasic, biphasic, triphasic, etc., with each phase amplitude and duration independently controllable, as is known in the art.

AC/DC shock selection module 146 can analyze various parameters to determine an appropriate arrhythmia therapy response. For instance, AC/DC shock selection module 146 can consider whether the arrhythmia is an atrial arrhythmia and/or a ventricular arrhythmia. For example, ventricular fibrillation tends to have major negative affects on the patient much sooner than atrial fibrillation. Accordingly, some implementations of AC/DC shock selection module 146 can employ a different therapy protocol for atrial fibrillation than for ventricular fibrillation. In one such case, the AC/DC shock selection module 146 can employ AC interferential shock therapy for atrial fibrillation. In this example the AC/DC shock selection module 146 can employ DC shocking therapy for ventricular fibrillation. In one variation, upon detection of ventricular fibrillation, the AC/DC shock selection module 146 can apply AC interferential preconditioning for a duration sufficient to charge components such as capacitors required for delivering DC shocking therapy, wherein the component preferably charges while the AC signals are being delivered.

Some implementations of AC/DC shock selection module 146 can employ tiered therapy to address detected arrhythmias. For example, the AC/DC shock selection module 146 can apply AC interferential therapy to an affected region of the heart and monitor an effectiveness of the therapy. If the arrhythmia has not been corrected after a predetermined time the AC/DC shock selection module 146 can switch to a DC therapy. In such an instance where the AC interferential therapy was not effective in correcting the arrhythmia it may still be effective in preconditioning the affected region such that a relatively low power DC therapy can be applied. In a tiered system, the predetermined time for atrial conditions can be different than for ventricular conditions.

Other implementations can include feedback loops to provide information for future therapy. For instance, the AC/DC shock selection module 146 can analyze IEGM data obtained during interferential energizing or therapy. From analyzing the IEGM data the AC/DC shock selection module 146 can determine how long the AC signals were delivered before an effective beat frequency develops and/or how long it takes for the beat frequency takes to depolarize the target cardiac tissue. Stated another way, the AC/DC shock selection module 146 can determine a length of time before the interferential therapy affects the target tissue. This information can then be utilized in future arrhythmia scenarios to select a particular AC and/or DC therapy.

Still another implementation can deliver the AC signals just long enough to simulate a specific waveform, such as biphasic or triphasic. Such an implementation can simulate the specific waveform with reduce risk of refibrillation. Another variation can apply the AC signal first to one pathway, and then while that pathway is still active, the second pathway may be activated with the AC signal. Such an implementation may make it easier to control the actual waveform created in the heart, such as forcing polarity or number of phases created by the interference pattern.

In instances where the AC/DC shock selection module 146 selects AC shocking, the AC shock(s) is delivered as a combination of at least two AC signals that are concurrently delivered. Each AC signal is delivered via electrodes interposed around the target tissue. Various examples of suitable electrodes are described above in relation to FIG. 1.

In instances where the AC/DC shock selection module 146 selects AC preconditioning, the AC/DC shock selection module 146 causes AC signals to be supplied to cause interferential preconditioning prior to delivery of the DC shocking pulse. This technique can greatly reduce DC shocking energy and resultant side affects. In one example, interferential preconditioning is provided across first and second pathways using AC signals having voltages in the range of about 5 volts to about 50 volts, after which DC shocks of less than about 5 joules, and preferably less than 2 joules, can sufficiently depolarize target cardiac tissue. Of course, higher DC shocking energies can follow interferential preconditioning, though increased side affects may be experienced.

In instances where the AC/DC shock selection module 146 selects DC shocking therapy, the system will monitor the last effective therapy. If the DC shock energy is above a predefined threshold (5J for example), the system will adjust either the medium frequency AC stimulation, or the beat frequency of the AC stimulation to better optimize the efficacy of the AC stimulation.

In instances where the AC/DC shock selection module 146 selects DC shocking therapy, the DC shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

In cases where DC shocking is delivered, cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be disorganized to a degree that makes synchronization more difficult).

In low-energy cardioversion, an IMD typically delivers a cardioversion stimulus (e.g., 0.1-5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways. In any of the above mentioned DC shock therapies, the AC/DC shock selection module 146 can interferentially energize the target tissue while charging the DC shocking components such as capacitors. This interferential energizing may be applied synchronously or asynchronously with the intrinsic cardiac signal.

Exemplary External Medical Device

Figure 3:
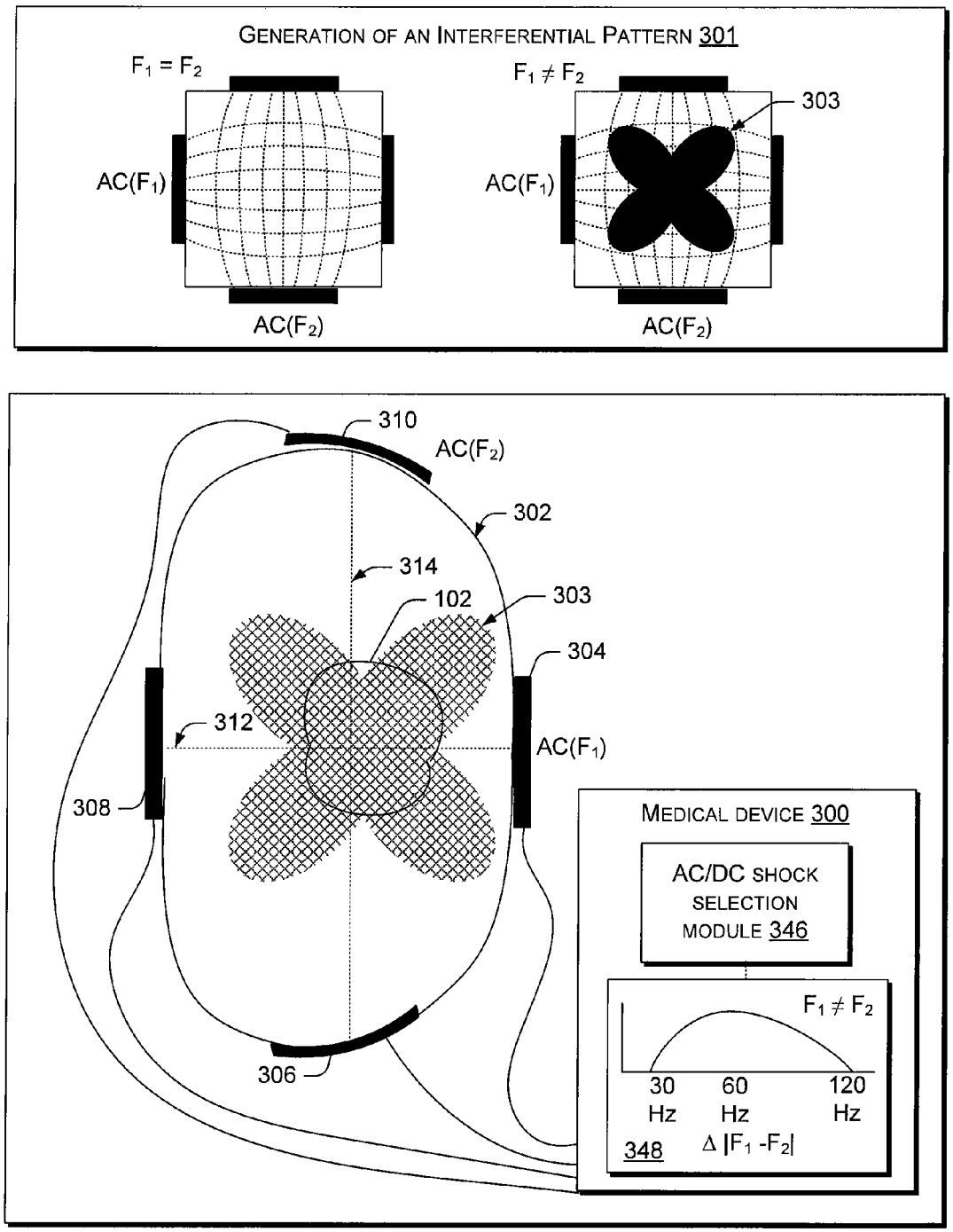
FIG. 3 is a simplified diagram illustrating interferential techniques and an exemplary external medical device operable to employ techniques for interferential cardiac preconditioning and depolarization in accordance with one implementation.

FIG. 3 shows generation of an interferential pattern 301 and an exemplary medical device 300 that in this instance is implemented as a defibrillator, but can assume various other form factors in other implementations. For instance, the medical device can be implemented in connection with any medical device that is configured or configurable to non-invasively sense cardiac data and/or provide cardiac therapy. Note that while the medical device itself is external to the patient, the medical device can in some configurations be coupled to, or in communication with, various sensors, electrodes, or implanted medical devices to achieve a desired functionality.

In FIG. 3, generation of an interferential pattern 301 is shown. Where two AC signals are delivered at the same frequency ($F_1=F_2$), no significant interferential pattern develops. However, when the frequencies differ ($F_1 \neq F_2$), then an interferential pattern 303 develops.

In FIG. 3 the patient's heart 102 is shown within the thorax 302. Four electrodes 304, 306, 308, and 310 are positioned proximate an outer surface of the patient's skin and are connected to medical device 300.

Medical device 300 is configured to detect cardiac arrhythmias and to employ a responsive therapy for the purpose of converting the arrhythmia to a more normal cardiac rhythm. To this end, medical device 300 includes an AC/DC shock selection module 346 that is operable to ascertain when a detected patient condition warrants one or both of atrial and ventricular shock therapy. In such an instance, AC/DC shock selection module is operable to select an appropriate shocking therapy including DC shock therapy, AC shock therapy, and DC shock therapy with AC preconditioning.

As described herein, an exemplary implantable device can include an arrhythmia detection module configured to detect a cardiac arrhythmia; an AC shock module configured to call for delivery of a shock therapy regimen that relies on delivery of one or more AC shocks; a DC shock module configured to call for delivery of a shock therapy regimen that relies on delivery of one or more DC shocks; an AC preconditioning and DC shock module configured to call for delivery of a shock therapy regimen that relies on delivery of AC preconditioning therapy followed by one or more DC shocks; and a shock selection module configured to select one of the shock modules responsive to a detected cardiac arrhythmia. In such a device, the shock selection module can be configured to select the shock module based at least in part upon whether the detected cardiac arrhythmia is an atrial arrhythmia or a ventricular arrhythmia. Further, the shock selection module can be configured to select electrodes for delivery of a shock therapy regimen (e.g., based on the location and/or type of arrhythmia). Also, the device may be configured to deliver AC preconditioning therapy while charging components to deliver DC shocks.

In the example of FIG. 3, the module 346 is shown along with a plot 348 of effectiveness and frequency difference. The module 346 may include a processor-executable selection algorithm or instructions, processor-executable instructions to call for delivery of a shock therapy regimen and optionally processor-executable instructions for delivery of a shock therapy regimen. With respect to the plot 348, as various studies have shown, an AC signal at 60 hertz current may induce VF more readily than an AC signal at frequencies in a range of about 30 hertz to about 120 hertz and other than 60 hertz. Hence, the module 346 may set or adjust the offset to achieve a desired result. Further, the module 346 may rely on sensed cardiac information as feedback to set or adjust one or more AC signal parameters (e.g., delivery electrode(s), current(s), voltage(s), frequency(ies), etc.).

AC shock therapy and/or AC preconditioning is accomplished as described above via delivery of two concurrent intersecting AC signals to create interferential energizing of target cardiac tissue. As used herein, concurrent means that the two signals are concurrent for at least a portion of their duration, but do not necessarily start and/or end at the same time. In the illustrated configuration, a first AC signal can be delivered along a first pathway 312 between electrodes 304 and 308 and the second signal can be delivered between electrodes 306 and 310 along a second pathway 314. Where the frequencies differ, the interferential pattern 303 is formed in the body.

In the example of FIG. 3, other electrode configurations can alternatively be employed. For instance, more than two electrodes can be involved in delivering a particular one of the AC signals. In another example, a single electrode can be involved in delivering both signals. In other instances more than two AC signal can be delivered. In still other cases, electrodes can be dedicated to treating particular regions of the heart. For instance, the four electrodes (304-310) illustrated in FIG. 3 can lie in an axial plane that passes through the ventricles and another set of electrodes can be positioned on an axial plane that passes through the atria. Viewed another way, the particular device setup is not critical; instead the main point is to cause a beat frequency to occur proximate the target tissue that interferentially energizes the target tissue. Characterized another way, the interferential energizing can be thought of as creating a virtual electrode on the target tissue.

Examples of various frequency ranges for the AC signal delivered to the target tissue are described above in relation to the implantable medical device configuration of FIGS. 1-2. These frequency ranges can also be employed by external device 300. Some implementations can utilize frequencies toward the upper end of the frequency ranges as higher frequencies are relatively less negatively affected by high resistance which can be encountered as the signals pass through the patient's skin. In one such example, AC signal frequencies of 4,000 hertz and 4,100 hertz can be selected to generated an interferential beat frequency of about 100 hertz.

As described herein, for skin mounted electrodes, the frequency range is typically greater than for electrodes placed in the body (e.g., consider dielectric properties and number and type of material layers involved as conductive media, etc.). For example, skin mounted electrodes may deliver frequencies in the range of about 4 kHz to about 5 kHz while in vivo electrodes may delivery energy in a manner that differs from the skin mounted electrodes (e.g., due to dielectric properties and impedance concerns). In an example, internal electrodes (e.g., in vivo) may delivery energy in a frequency range of about 4 kHz to about 6 kHz. As mentioned, for offset, a range of about 30 Hz to about 120 Hz may be used with 60 Hz being a likely maximum for effectiveness.

With respect to voltage, skin mounted electrodes can be expected to require higher voltages that in vivo electrodes. For example, a skin mounted array may require about 50 V while an in vivo electrode array may require less voltage (e.g., about 5V to about 15 V).

As described herein, an exemplary method can deliver two or more alternating signals with an offset frequency to precondition tissue for stimulation with a pulse (e.g., a shock) where the preconditioning can reduce pain associated with the stimulation. For treatment of certain conditions, such as VT or VF, corrective stimulation/shock energy should be delivered as soon as possible (e.g., within 20 seconds of detection). Hence, delivery of interferential preconditioning energy should not significantly delay corrective action. However, for atrial arrhythmias, the time for corrective action is not as critical as for ventricular arrhythmias. Thus, an exemplary method can deliver interferential preconditioning energy for a longer period of time before delivering corrective action. For example, for treatment of an atrial arrhythmia, preconditioning energy may be delivered for about two minutes prior to energy aimed specifically at terminating the atrial arrhythmia. Such an extended period of preconditioning can help minimize pain associated with energy aimed specifically at terminating an atrial arrhythmia.

With respect to pain thresholds, a typical patient is likely to experience pain for any energy above about 2 J. However, it can be possible to precondition and "treat" an arrhythmia using interferential energy in a manner that allows for subsequent termination of the arrhythmia using a low-energy stimulation technique. Further, if the subsequent technique fails, a higher energy technique may be delivered. Again, as atrial arrhythmias are typically not as life threatening as ventricular arrhythmias, various techniques can be readily tiered and delivered over a period of minutes for treatment of atrial arrhythmias. In contrast, for serious ventricular arrhythmias, any tiered approach should aggressively ramp up to a high energy approach in about less than a minute (e.g., if lower tiers fail to terminate the arrhythmia).

First Exemplary Method

Figure 4:
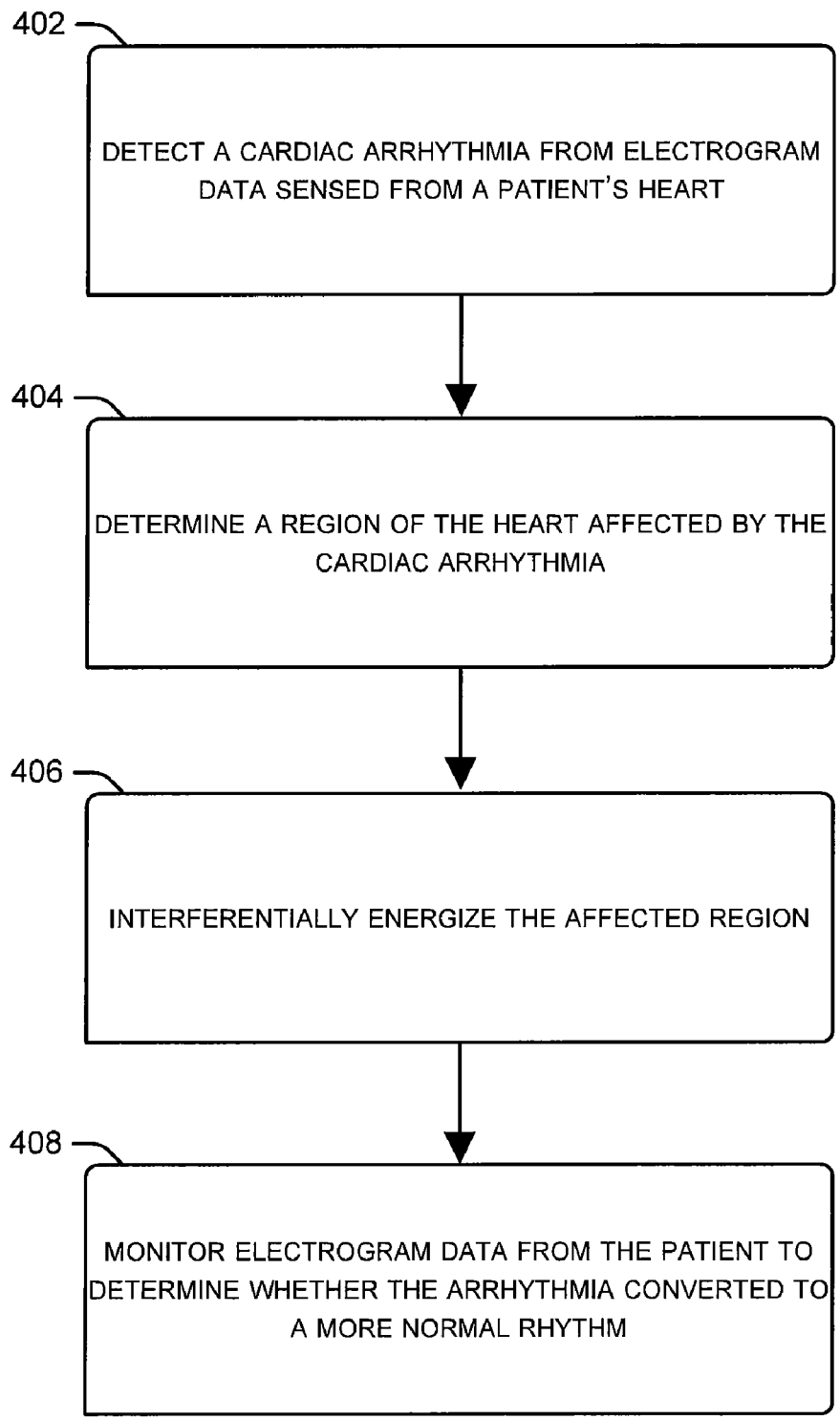
FIG. 4 is a flowchart of an exemplary technique for interferential cardiac therapy in accordance with one implementation.

FIG. 4 is a flow diagram of a method or technique 400 for activating specific IMD electrodes from a set of available electrodes. The order in which the method is described is not intended to be construed as a limitation, and any number of the described blocks can be combined in any order to implement the technique, or an alternate technique. Furthermore, in some instances, the method can be implemented in any suitable hardware, software, firmware, or combination thereof employed by a computing device such as an implantable medical device (IMD), an external medical device, or a system, such as a system including both internal and external medical devices. In such a scenario, the method can be stored as a set of instructions on a computer readable storage media for execution by the computing device.

At block 402, the technique detects a cardiac arrhythmia from electrogram data sensed from a patient's heart. Various known techniques can be employed for detecting the arrhythmia. These techniques and/or other techniques can be utilized to determine a region of the heart affected by the cardiac arrhythmia at block 404.

The region is interferentially energized at block 406. Interferentially energizing utilizes superposition of two (or more) medium to high frequency AC signals that are offset by a relatively small frequency. The superposition creates a beat frequency corresponding to the offset as the two signals go in and out of phase. In some cases, interferentially energizing is utilized to precondition target cardiac tissue sufficiently to lower the cardiac tissue's activation threshold but not to depolarize the cardiac tissue; this is followed with a DC shock that may be delivered synchronously with the preconditioning waveform; the preconditioning waveform may be discontinued prior to or simultaneous with delivery of the DC shock. In other cases, interferentially energizing the target tissue stimulates the target cardiac tissue sufficiently to cause depolarization. In essence, interferential energizing creates a virtual electrode on the target region delivering signals at the beat frequency.

Electrogram data from the patient is monitored to determine whether the arrhythmia converted to a more normal rhythm at block 408. In an instance where conversion did not occur, interferential energizing can be continued or another therapy such as DC shocking can be employed. In instances where the interferential energizing lowered the activation threshold of cardiac muscle cells within the region, but did not cause depolarization then DC shocking therapy can be affective at lower energy levels than would otherwise be affective. In one such example, the target tissue is interferentially energized in a range of about 5-15 volts for a period of about 5 to 20 seconds and then shocked with a DC pulse of about 2 joules; the preconditioning waveform may be discontinued prior to or simultaneous with delivery of the DC shock. The skilled artisan should recognize other configurations.

This description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

CONCLUSION

Interferential energizing or interferential therapy of cardiac target tissue can be thought of as creating a virtual electrode on the target tissue which energizes the target tissue at a beat frequency. The beat frequency is established by a frequency difference between two AC signals concurrently directed toward the cardiac target tissue. Interferential energizing can be utilized to depolarize target tissue and/or to precondition the target tissue so that subsequent, relatively low power DC pulse can depolarize the target tissue.

What is claimed is:

1. A medical device comprising:
    a plurality of electrodes configured for placement adjacent cardiac tissue;
    a sensing circuit configured to sense cardiac electrogram signals through one or more of the electrodes;
    an arrhythmia detection module configured to process detected cardiac electrogram signals and detect for a cardiac arrhythmia;
    an AC shocking circuit configured to concurrently deliver first and second alternating current (AC) signals having a frequency difference of about 50 hertz to about 200 hertz to cardiac tissue through one or more of the electrodes, wherein the AC signals are configured such that the concurrent delivery thereof preconditions the cardiac tissue to lower the activation threshold of the cardiac tissue without causing depolarization of the cardiac tissue;
    a DC shocking circuit configured to deliver a direct current (DC) signal to cardiac tissue through one or more of the electrodes, wherein the DC signal is configured such that delivery thereof depolarizes the cardiac tissue; and
    a microcontroller configured to, upon detection of a cardiac arrhythmia, cause the AC shocking circuit to deliver multiple cycles of the first and second AC signals, and cause the DC shocking circuit to deliver a DC signal after delivery of the AC signals.

2. The medical device of claim 1, wherein the arrhythmia detection module is configured to detect atrial arrhythmias, ventricular arrhythmias or atrial arrhythmias and ventricular arrhythmias.

3. The medical device of claim 1 comprising an implantable medical device (IMD).

4. The medical device of claim 1 comprising an external defibrillator.

5. The device of claim 1 wherein the first and second AC signals have voltages in a range of about 5 volts to about 15 volts and the DC signal provides energy less than about 5 joules.

6. The device of claim 1 wherein the first and second AC signals are delivered for about 5 seconds to about 20 seconds.

7. The device of claim 1 wherein the DC shocking circuit comprises a component that requires charging, and the first and second AC signals are delivered at least for a duration required to charge the component.

8. The device of claim 1 wherein the DC shocking circuit comprises a component that require charging, and the component is charged while the first and second AC signals are delivered.

9. A medical device comprising:
    a plurality of electrodes configured for placement adjacent cardiac tissue;
    a sensing circuit configured to sense cardiac electrogram signals through one or more of the electrodes;
    an arrhythmia detection module configured to process detected cardiac electrogram signals and detect for a cardiac arrhythmia;
    an AC shocking circuit configured to concurrently deliver first and second alternating current (AC) signals having a frequency difference of about 50 hertz to about 200 hertz to cardiac tissue through one or more of the electrodes, wherein the AC signals are configured such that the concurrent delivery thereof preconditions the cardiac tissue to lower the activation threshold of the cardiac tissue without causing depolarization of the cardiac tissue;
    a DC shocking circuit configured to deliver a direct current (DC) signal to cardiac tissue through one or more of the electrodes, wherein the DC signal is configured such that delivery thereof depolarizes the cardiac tissue; and
    a microcontroller configured to, upon detection of a cardiac arrhythmia, cause the AC shocking circuit to deliver multiple cycles of the first and second AC signals, and cause the DC shocking circuit to deliver a DC signal after delivery of the AC signals; wherein,
    the plurality of electrodes comprises an electrode configured to be positioned in a patient's superior vena cava, an electrode configured to be positioned in the patient's vasculature over the left ventricle, an electrode configured to be positioned in the patient's right ventricle, and a housing of the medical device;
    the first AC signal is delivered using the electrode configured to be positioned in the superior vena cava and the electrode configured to be positioned in vasculature over the left ventricle; and the second AC signal is delivered using the electrode configured to be positioned in the right ventricle and the housing of the medical device.

10. A medical device comprising:

a plurality of electrodes configured for placement adjacent cardiac tissue;

a sensing circuit configured to sense cardiac electrogram signals through one or more of the electrodes;

an arrhythmia detection module configured to process detected cardiac electrogram signals and detect for a cardiac arrhythmia;

an AC shocking circuit configured to concurrently deliver first and second alternating current (AC) signals having a frequency difference of about 50 hertz to about 200 hertz to cardiac tissue through one or more of the electrodes, wherein the AC signals are configured such that the concurrent delivery thereof preconditions the cardiac tissue to lower the activation threshold of the cardiac tissue without causing depolarization of the cardiac tissue;

a DC shocking circuit configured to deliver a direct current (DC) signal to cardiac tissue through one or more of the electrodes, wherein the DC signal is configured such that delivery thereof depolarizes the cardiac tissue; and a microcontroller configured to, upon detection of a cardiac arrhythmia, cause the AC shocking circuit to deliver multiple cycles of the first and second AC signals, and cause the DC shocking circuit to deliver a DC signal after delivery of the AC signals, wherein, the plurality of electrodes comprises an electrode configured to be positioned in a patient's superior vena cava, an electrode configured to be positioned in the patient's right ventricle, an electrode configured to be positioned in the patient's coronary sinus, and a housing of the medical device;

the first AC signal is delivered using the electrode configured to be positioned in the superior vena cava and the electrode configured to be positioned in the right ventricle; and the second AC signal is delivered using the electrode configured to be positioned in the coronary sinus and the housing of the medical device.

* * * * *